(12) United States Patent
McCauley (10) Patent No.: US 9,170,241 B2
(45) Date of Patent: Oct. 27, 2015

(54) EVACUABLE INLET FOR GAS CHROMATOGRAPH INJECTOR

(71) Applicant: Edward B. McCauley, Cedar Park, TX (US)

(72) Inventor: Edward B. McCauley, Cedar Park, TX (US)

(73) Assignee: Thermo Finnigan LLC, San Jose, CA (US)

( * ) Notice: Subject to any disclaimer, the term of this patent is extended or adjusted under 35 U.S.C. 154(b) by 228 days.

(21) Appl. No.: 13/788,207

(22) Filed: Mar. 7, 2013

(65) Prior Publication Data
US 2014/0250978 A1    Sep. 11, 2014

(51) Int. Cl.
| | | |
|---|---|---|
| *G01N 30/16* | (2006.01) | |
| *G01N 30/26* | (2006.01) | |
| G01N 30/12 | (2006.01) | |
| G01N 30/18 | (2006.01) | |
| G01N 30/54 | (2006.01) | |

(52) U.S. Cl.
CPC ............... *G01N 30/16* (2013.01); *G01N 30/26* (2013.01); *G01N 30/12* (2013.01); *G01N 30/18* (2013.01); *G01N 30/54* (2013.01)

(58) Field of Classification Search
CPC .... G01N 30/30; G01N 30/461; B01J 2220/54
See application file for complete search history.

(56) References Cited

U.S. PATENT DOCUMENTS

| | | | |
|---|---|---|---|
| 3,247,704 A | | 4/1966 | Koenig |
| 3,847,546 A | * | 11/1974 | Paul .............................. 73/23.35 |
| 4,096,734 A | * | 6/1978 | Khayat ......................... 73/23.41 |
| 6,017,414 A | * | 1/2000 | Koemtzopoulos et al. ......................... 156/345.25 |
| 6,402,947 B1 | * | 6/2002 | Altamirano et al. ........ 210/198.2 |
| 8,308,854 B2 | | 11/2012 | McCauley et al. |
| 8,371,152 B2 | | 2/2013 | McCauley et al. |
| 2010/0251896 A1 | | 10/2010 | Kellogg |
| 2011/0138877 A1 | | 6/2011 | McCauley et al. |

FOREIGN PATENT DOCUMENTS

| | | |
|---|---|---|
| EP | 0770869 A2 | 5/1997 |
| EP | 2317309 A1 | 5/2011 |
| FR | 2 928 733 A1 | 9/2009 |

(Continued)

OTHER PUBLICATIONS

Extended European search report for EP application 14158297.3, EPO Munich, Germany, Jun. 6, 2014, pp. 1-5.

(Continued)

*Primary Examiner* — Laura Martin
*Assistant Examiner* — Alex Devito
(74) *Attorney, Agent, or Firm* — Thomas F. Cooney (57) ABSTRACT

A gas chromatography (GC) system comprises: a sample injector adapted to receive a liquid sample into an interior cavity thereof and to volatilize the liquid sample; a GC column configured to receive the volatilized sample from the sample injector; a carrier gas inlet line fluidically coupled to a gas inlet port of the sample injector; a septum purge vent line fluidically coupled to a first gas outlet port of the sample injector; a split-flow vent line fluidically coupled to a second gas outlet port of the sample injector; and a vacuum system configured to apply vacuum to the septum purge vent line, the split-flow vent line and the interior cavity of the sample injector. Alternatively, the vacuum system may be coupled to a vacuum port of the sample injector. A separate flow of helium gas may be supplied to an inlet of the GC column.

29 Claims, 6 Drawing Sheets

(56) References Cited

FOREIGN PATENT DOCUMENTS

| WO | WO 2005/116627 A1 | 12/2005 |
| WO | WO 2011/092724 A1 | 8/2011 |

OTHER PUBLICATIONS

K. Grob, "Split and Splitless Injection for Quantitative Gas Chromatography: Concepts, Processes, Practical Guidelines, Sources of Error", 4th ed., Wiley-VCH Verlag GmbH, 2001, Appendix 3, pp. 448-452.

K. Grob, "Split and Splitless Injection for Quantitative Gas Chromatography: Concepts, Processes, Practical Guidelines, Sources of Error", 4th ed., Wiley-VCH Verlag GmbH, 2001, Chapter C Split Injection, pp. 149-155.

R.L. Grob and E.F. Barry, eds., "Modern Practice of Gas Chromatography", 4th ed., John Wiley & Sons, 2004, Chapter 9, pp. 461-489.

R.L. Grob and E.F. Barry, eds., "Modern Practice of Gas Chromatography", 4th ed., John Wiley & Sons, 2004, Introduction, pp. 1-21.

\* cited by examiner

EVACUABLE INLET FOR GAS CHROMATOGRAPH INJECTOR

FIELD OF THE INVENTION

This invention relates to gas chromatography and, more particularly, to conservation of gases used as carrier gases in gas chromatograph injectors and columns.

BACKGROUND OF THE INVENTION

Traditional split/splitless (SSL) or programmed temperature vaporizing (PTV) injection ports for gas chromatographs typically consume large volumes of carrier gas by virtue of what is used at the split vent and septum purge vent rather than what is utilized for the actual analytical separation (column flow). To illustrate, a capillary column flow of approximately 1 standard cubic centimeter per minute (sccm) may have 50 sccm or more of split flow and 5 sccm of septum purge flow. One prior art method to reduce this consumption, e.g., "gas saver", can reduce the split flow following an injection period. Reducing the split flow to too low a value, however, can result in undesirable elevated baselines. This may be caused by a continual outgassing of higher molecular weight contaminants introduced from the sample matrix, outgassing of polymeric seals such as O-rings, injection port septa and/or coring of such septa, or be caused by oxidation of the column stationary phase due to larger concentrations of oxygen which has back-diffused through the septum. Reducing these contaminants has traditionally been accomplished through dilution by using large split flows. Thus, significant quantities of carrier gas may be consumed, even during chromatograph idle periods.

Figure 1:
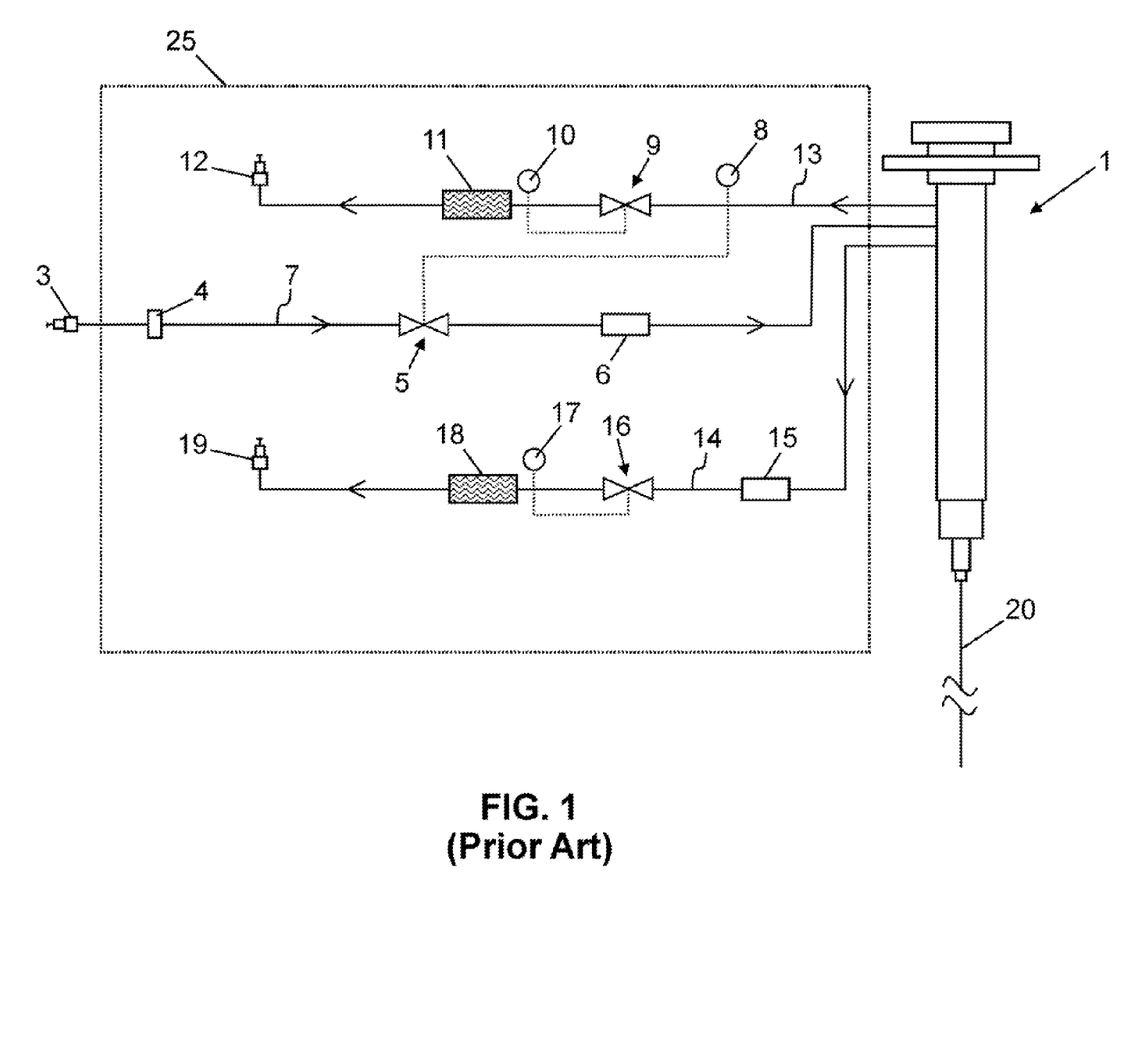
FIG. 1 shows a conventional gas supply and exhaust system and Split/Splitless injector for a gas chromatograph.

FIG. 1 illustrates a conventional gas supply and exhaust system 25 and associated split/splitless injector 1 of the prior art. The split/splitless (SSL) injector 1 is provided for receiving injections of liquid samples from a syringe (not illustrated), for flash vaporizing the liquid samples by application of heat, for mixing the volatilized sample material with a carrier gas and for providing a portion of the volatilized sample material to a gas chromatograph column 20. The carrier gas supply, e.g. helium, is introduced under pressure into a gas inlet line 7 by means of a gas fitting 3. A controlled pressure of the carrier gas is provided to the injector by an electronic pressure controller (not shown) which results in a controlled flow of carrier gas through column 20. A fine porosity filter 4, e.g. a stainless steel fit, removes any particulate matter that may foul operation of a proportional valve 5 that is disposed downstream in the gas inlet line 7. The proportional valve 5 maintains a setpoint pressure within the body of the injector 1 in response to measurements provided by pressure sensor 8 in order to establish a calculated flow in the analytical column in accordance with the Poiseuille equation. The pressure sensor 8 provides a feedback loop to a control circuit of the electronic pressure controller. Optionally, a chemical trap 6 is included in the gas inlet line 7 to scrub the carrier gas of potential contaminants, e.g. hydrocarbons and/or oxygen.

As is known, generally only a portion (and, frequently, only a small portion) of the volatilized sample material and carrier gas flow actually enters the column 20. The remainder of the volatilized sample material and carrier gas flow is exhausted from the system by means of septum purge vent line 13 and, frequently, split flow vent line 14. Flow restrictor 11 and flow restrictor 18, disposed, respectively, in the septum purge vent line 13 and split flow vent line 14 maintain a pressure difference between the exhaust ports 12, 19, which are at ambient pressure, and the higher-pressure segments of the vent lines 13, 14 that are adjacent to the injector 1. Pressure sensors 10, 17 measure the pressures of the high-pressure segments of the vent lines 13, 14. This information is provided as continuous feedback to the electronic pressure controller which calculates the pressure differences across the flow restrictors 11, 18 and operates the proportional valves 9, 16 so as to maintain desired flow rates within the vent lines 13, 14, in accordance with a mathematical calculation or calibrated lookup table. A chemical trap 15 may be included in the split flow vent line 14 to protect the proportional valve 16 from contamination by various oils and greases that may volatilize from the sample or outgas from injector components. Another similar chemical trap (not shown) may also be included in the septum purge vent line 13.

The injector 1 includes two basic modes of operation: split and splitless. In the split injection mode, a split flow is established that exits the split vent line 14. This mode of operation is used for injection of concentrated analytes to prevent overloading of the column or saturation of the detection system used at the terminal end of the column. In the splitless mode of operation, the split vent line 14 is closed (i.e., proportional valve 16 is closed) during a sample injection to cause the bulk of the sample material to be transferred to the capillary column. After a specified time interval, the split vent, line is once again opened to vent residual solvent vapors and to dilute any contaminants that might outgas from contaminated surfaces.

In both the split and splitless modes, far greater amounts of carrier gas are used for split flow and septum purge flow than are required for the gas chromatography (GC) column flow carrying out the analytical separation. During idle times following a split or splitless injection, large volumes of split flow are typically maintained to dilute outgassing of residual contaminants. Even during idle times, when the chromatography system is not in use and the column is cooled to room temperature, the injector remains at above-ambient temperature and under a continued flow of gas. This results in a large consumption of high purity gas, e.g. helium.

Helium, which is a finite natural resource, is becoming increasingly expensive and difficult to procure in some areas of the world. Helium is often the preferred gas of choice due to sensitivity, efficiency, chemical inertness, safety or other concerns. Alternative carrier gasses, e.g. hydrogen or nitrogen, can be used in some instances. For a mass spectrometer detection based system, hydrogen decreases sensitivity for electron ionization (EI) and can cause dehydrohalogenation reactions in the ion source while nitrogen can result in charge exchange reactions, and is known to be less efficient as a carrier gas. Thus, there is a need in the art for gas chromatography systems that conserve helium by restricting the times at which helium gas flow is applied to only those times when such helium flow is required and by restricting the flow rate of helium at such times to be not significantly greater than the minimum flow rate required.

SUMMARY

The inventor of the present invention has realized that many of the beneficial aspects associated with the flow of helium and other carrier gases through a chromatography injector can be achieved, during injector idle or standby times, by simply discontinuing the flow of carrier gas and, instead, applying vacuum to the injector. Accordingly, an injector (or injection port) for a gas chromatograph/mass spectrometer may be configured to allow vacuum to be applied to the septum purge vent and split flow vent while simultaneously disabling the flow of carrier gas. This allows for conserving helium gas while the instrument is in a standby condition, without the risk of column oxidation. Additionally, since no gas load is applied, power can also be conserved by switching off a roughing pump (such as a rotary vane mechanical pump) while a high-vacuum pump (such as a turbomolecular pump or an oil diffusion pump) remains active. In some embodiments, a small residual purge gas flow may be delivered to the injector inlet line or a helium was flow may be delivered to the column inlet. This enables a high temperature low pressure bakeout of inlet components. An electronic controller can execute the operations of bakeout and/or standby in an automated fashion, ensuring the foreline pressure has dropped to a minimal value, before the mechanical pump is disabled. The controller can restart the mechanical pump if the pressure rises to a predetermined threshold, or allow it to remain on if the cycling rate is excessive due to a leak in the system (e.g. an excessively cored septum). The disclosed apparatus allows shutting off the helium carrier gas to a chromatograph in order to reduce helium consumption during non-runtime, without risk of undue oxidation of the GC column. Additionally, overall system power consumption may also be reduced and the inlet can be efficiently cleaned by application of heat and vacuum.

Accordingly, in a first aspect of the present teachings, a gas chromatography (GC) system comprises: a sample injector adapted to receive a liquid sample into an interior cavity thereof and to volatilize the liquid sample; a GC column configured to receive the volatilized sample from the sample injector; a carrier gas inlet line fluidically coupled to a gas inlet port of the sample injector; a septum purge vent line fluidically coupled to a first gas outlet port of the sample injector; a split-flow vent line fluidically coupled to a second gas outlet port of the sample injector; and a vacuum system configured to apply vacuum to the septum purge vent line, the split-flow vent line and the interior cavity of the sample injector.

According, to a second aspect of the present teachings, a gas chromatography (GC) system comprises: a sample injector adapted to receive a liquid sample into an interior cavity thereof and to volatilize the liquid sample; a GC column configured to receive the volatilized sample from the sample injector; a carrier gas inlet line fluidically coupled to a gas inlet port of the sample injector; a septum purge vent line fluidically coupled to a first gas outlet port of the sample injector; a split-flow vent line fluidically coupled to a second gas outlet port of the sample injector; and a vacuum system fluidically coupled to a vacuum port of the sample injector.

According to a third aspect of the present teachings, there is provided a method for operating a gas chromatography (GC) system comprising (a) a GC column within a heating oven and (b) a sample injector fluidically coupled to the GC column and having a carrier gas inlet port, a septum purge outlet port and a split-flow outlet port, wherein the method comprises: (i) discontinuing heating of the GC column by the heating oven; (ii) discontinuing the flow of a carrier gas into the carrier gas inlet port; and (iii) directing outputs of the septum purge outlet port and the split-flow vent outlet port to a vacuum system such that vacuum is applied to an interior cavity of the injector. The method may further comprise: (iv) providing helium gas so as to flow circumferentially around an exterior surface of the GC column in a direction generally towards an inlet of the GC column such that a portion of the helium gas enters the column inlet.

According to another aspect of the present teachings, there is provided a method for operating a gas chromatography (GC) system comprising (a) a GC column within a heating oven and (b) a sample injector fluidically coupled to the GC column and having a carrier gas inlet port, a septum purge outlet port, a split-flow outlet port and a vacuum port, wherein the method comprises: (i) discontinuing heating of the GC column by the heating oven; (ii) discontinuing a flow of a carrier gas into the carrier gas inlet port; closing the septum purge outlet port and the split-flow vent outlet port so as to prevent gas flow therethrough; and (iii) placing the vacuum port into fluidic communication with a vacuum system such that vacuum is applied to an interior cavity of the injector. The method may further comprise: (iv) providing helium gas so as to flow circumferentially around an exterior surface of the GC column in a direction generally towards an inlet of the GC column such that a portion of the helium gas enters the column inlet.

According to yet another aspect of the present teachings, there is provided a method for operating a gas chromatography (GC) system comprising (a) a GC column within a heating oven and (h) a sample injector fluidically coupled to the GC column and having a carrier gas inlet port, a septum purge outlet port and a split-flow outlet port, wherein the method comprises: (i) discontinuing the flow of a carrier gas into the carrier gas inlet port; (ii) directing outputs of the septum purge outlet port and the split-flow vent outlet port to a vacuum system such that vacuum is applied to an interior cavity of the injector, wherein the heating oven is maintained at an above-ambient operating temperature; and (iii) providing helium gas so as to flow circumferentially around an exterior surface of the GC column in a direction generally towards an inlet of the GC column such that a portion of the helium gas enters the column inlet. The flow rate of the helium gas may be chosen so as to be sufficient to prevent degradation of the GC column at the operating temperature but insufficient to prevent maintenance of vacuum within an interior cavity of the sample injector.

DETAILED DESCRIPTION

This disclosure describes improved as chromatograph injector systems and methods for operating gas chromatograph injectors. The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To more particularly appreciate the features of the present invention, the reader is referred to FIGS. 2 through 6 in conjunction with the following description.

Figure 2:
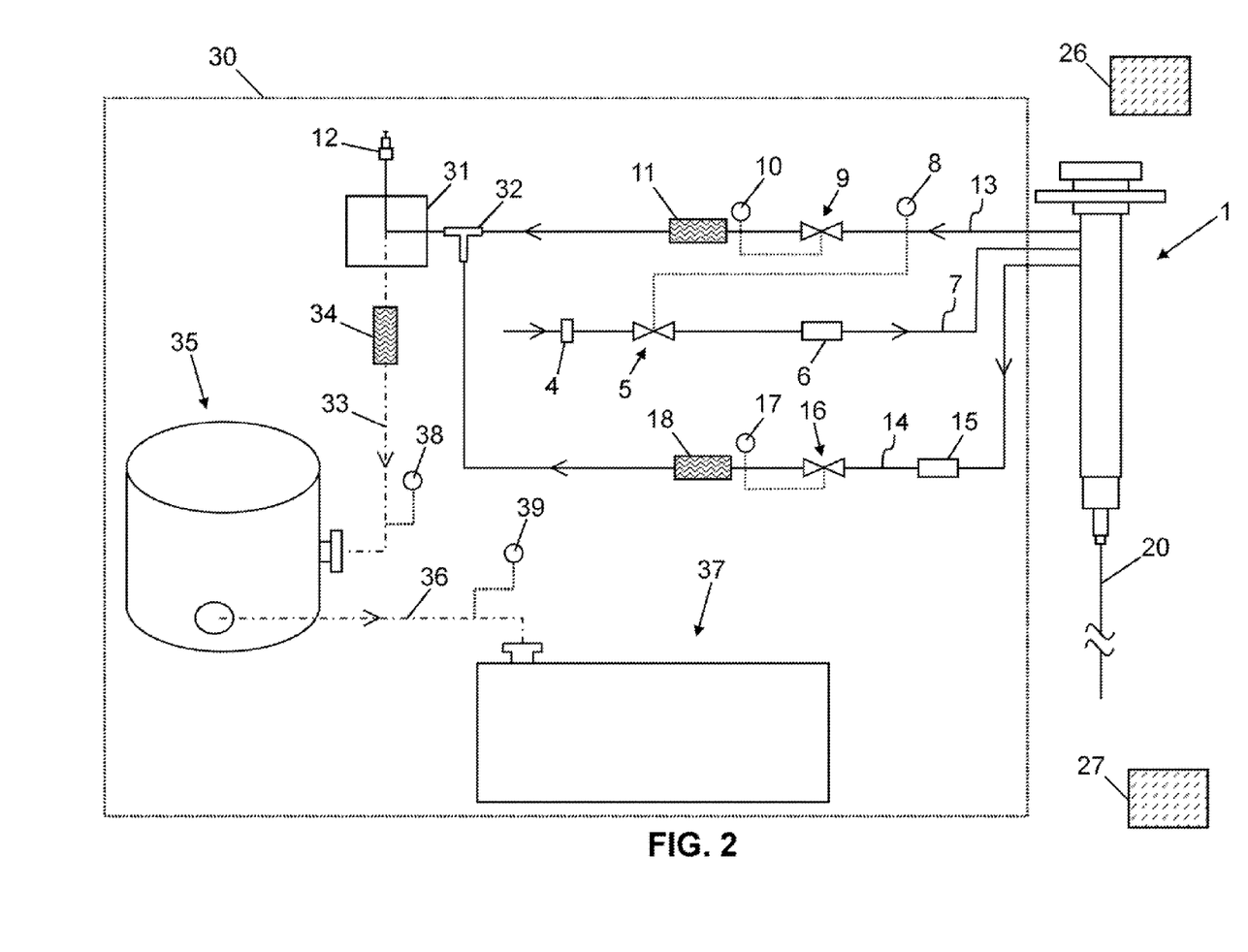
FIG. 2 illustrates a first gas supply and exhaust system for a gas chromatograph in accordance with an embodiment of the present teachings.

FIG. 2 illustrates a first gas supply and exhaust system 30 for a gas chromatograph in accordance the present teachings. Similarly to the conventional gas supply and exhaust system 25 illustrated in FIG. 1, the system 30 shown in FIG. 2 may be fluidically coupled to a split/splitless injector apparatus 1 by means of gas inlet line 7, septum purge vent line 13 and split-flow vent line 14. Various components that are numbered similarly in FIG. 1 and FIG. 2 have similar functions and, thus, the descriptions of such components are not repeated in detail here.

In contrast to the gas supply and exhaust system 25 illustrated in FIG. 1, the system 30 shown in FIG. 2, the vent lines 13, 14 do not have separate exhaust ports, but are, instead, fluidically coupled by a tee-junction 32 which is also fluidically coupled to a common port of a three-port valve 31. Another port of the three-port valve 31 is fluidically coupled to an exhaust port 12. The remaining port of the three-port valve is fluidically coupled to a vent port or interstage port of a turbomolecular pump 35 by means of vacuum line 33. The foreline port of the vacuum pump 35 exhausts to foreline 36 which fluidically couples the vacuum pump 35 to a low-vacuum or "roughing" pump 37 such as a rotary vane mechanical pump. A pressure sensor (vacuum sensor) 38 may monitor the pressure of the vacuum line 33; a second such sensor 39 may monitor the pressure of the foreline 36.

During normal operation of the injector, the three-port valve 31 is configured such that the flow from both the septum purge vent line 13 and the split-flow vent line 14 is directed to the single exhaust port 12. However, during system standby, after the gas chromatography column has been cooled, the three-port valve 31 may be configured such that the flow from both of the vent lines 13, 14 is directed into the vacuum line 33. At the same time as or just prior to the time that the three-port valve 31 is configured to send the venting gases to the vacuum line, the inlet line proportional valve 5 is closed, thus shutting off the flow of the carrier gas (typically helium). Under these conditions, all of the gas lines of the system 30 (other than the line connected to exhaust port 12) and the injector 1 itself are placed under vacuum. A flow restricting element 34 such as a frit, capillary or orifice may be added to line 33 in order to keep the critical foreline pressure of pump 35 from being exceeded. This novel configuration allows for conserving helium gas while the instrument is in a standby condition, without the risk of column oxidation. Additionally, since no gas load is applied, power can also be conserved by switching off the roughing pump 37 while the intermediate- or high-vacuum pump 35 remains active.

In some embodiments, a small residual purge gas flow may be delivered to the inlet line 7 of the system 30 by maintaining the proportional valve 5 in a slightly open condition. An electronic pressure controller 26 may monitor the pressure the sub-ambient pressure of the system recorded by pressure sensor 8 and/or pressure sensor 38 and may control the residual purge flow rate at a predetermined value by operating the proportional valve 5 so as to maintain a target pressure. With the injector maintained at operating temperature, this enables a high temperature, low pressure bakeout of inlet and injector components. An electronic controller 27 that is electronically coupled to the vacuum sensors 38, 39 can execute the operations of bakeout and/or standby in an automated fashion, ensuring the foreline pressure has dropped to a minimal value before the mechanical pump is disabled. The controller can restart the mechanical pump if the pressure rises to a predetermined threshold, or allow it to remain on if the cycling rate is excessive due to a leak in the system (e.g. an excessively cored septum).

Figure 3:
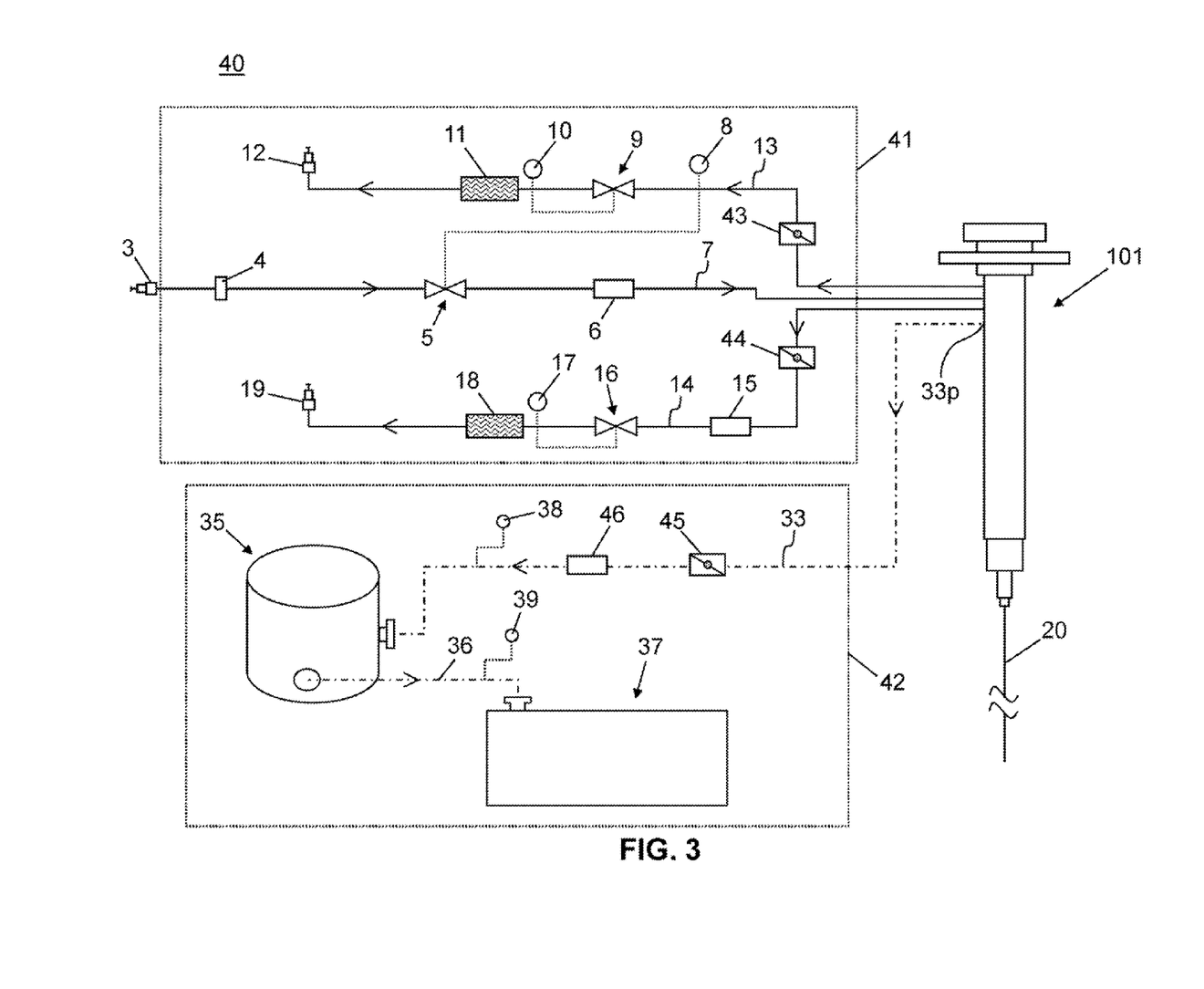
FIG. 3 illustrates a second gas supply and exhaust system for a gas chromatograph in accordance with an embodiment of the present teachings.

FIG. 3 illustrates a second gas supply and exhaust system for a gas chromatograph in accordance with an embodiment of the present teachings. The system 40 shown in FIG. 3 comprises a gas supply and exhaust sub-system 41 that is only slightly modified from a conventional system (e.g., see FIG. 1) and also comprises a separate vacuum sub-system 42. The injector 101 of the system 40 is modified, in comparison to a conventional injector, in that it comprises an additional vacuum port 33$p$ that fluidically couples the injector to a vacuum line 33 of the vacuum system 42. Thus, the vacuum sub-system 42 is not fluidically coupled to the gas supply and exhaust sub-system 41 other than possibly through the injector 101 as an intermediary component.

The gas supply and exhaust sub-system 41 of the system 40 (FIG. 3) may comprise shutoff valves 43, 44 disposed in the septum purge vent line 13 and split-flow vent line 14, respectively, so as to prevent suction from being applied to these lines during times that the injector 101 is under vacuum. Another shutoff valve (not shown) may optionally be installed in the gas inlet line 7 if either the proportional valve 5 or the chemical trap 6 is not suitable for use with vacuum. Likewise, the vacuum line 33 may also comprise another shutoff valve 45 to prevent vacuum from being applied to the injector 101 during injection periods or during column operation. A chemical trap 46 may be disposed in the vacuum line 33 so as to prevent back-diffusion of contaminants into the injector while it is under vacuum.

Other components of the system 40 have functions which are similar to the similarly numbered components shown in FIGS. 1-2 and the discussion of such components is not repeated here. As already discussed with reference to FIG. 2, an electronic pressure controller (not specifically shown) may monitor the pressure sensors and may operate the valves, accordingly, so as to maintain desired flow rates. A separate electronic controller (not shown) may perform similar functions with regard to the vacuum sub-system.

During normal operation of the injector 101 (FIG. 3), the shutoff valve 45 of the vacuum sub-system is closed and the shutoff valves 43, 44 of the gas supply and exhaust sub-system 41 are maintained open so that the septum purge vent line 13 and the split-flow vent line 14 perform their normal functions. However, during system standby, after the gas chromatography column has been cooled, the shutoff valves 43, 44 are closed. At the same time, the proportional valve 5 (or other shutoff valve) may be closed so as to stop the flow of helium from inlet line 7 into the injector. Either simultaneously or just subsequently, the shutoff valve 45 is opened so as to place the injector under vacuum. In some embodiments, a small residual purge gas flow may be delivered to the inlet line 7 of the system 30 while the injector is under vacuum by maintaining the proportional valve 5 in a slightly open condition. With the injector 101 maintained at operating temperature, application of vacuum to the injector in this fashion enables a high temperature, low pressure bakeout of inlet and injector components. It is understood that additional flow restricting elements may be placed in line 33 in order to keep the critical backing pressure of pump 35 from being exceeded when opening valve 45.

Certain embodiments of the instant invention may employ techniques and apparatus components as described in U.S. Pat. No. 8,371,152 titled "Helium Conservation Device for a Gas Chromatograph, said patent assigned to the assignee of the instant invention and incorporated herein by reference in its entirety. In brief, the aforementioned patent describes methods of purging a gas chromatograph system that include selecting between a first and a second mode. The first mode allows maximum helium conservation while the second mode allows minimum adverse effects on chromatographic methods, e.g. on retention times and detector responses.

According to the aforementioned U.S. patent, when maximum helium conservation is selected, an injector inlet is supplied with an auxiliary gas that is non-helium and the pressure of the non-helium gas is set to correspond to a given column flow. During an injection period, a helium flow from a gas inlet is established around the end of the analytical capillary column, wherein the helium flow is less than the column flow. Following the injection period, a helium flow is established around the end of the analytical capillary column, wherein the helium flow is greater than the column flow.

According to the aforementioned U.S. patent, when minimum method adverse effect is selected, the injector inlet is supplied with helium and the pressure of the helium gas is set to correspond to a given column flow. Dining an injection period, a helium flow from the second gas inlet is established around the inlet end of the analytical capillary column, wherein the coaxial helium flow is less than the column flow. Following the injection period, a helium flow is established around the inlet end of the analytical column, wherein the helium flow is greater than the column flow. The main injector inlet is then supplied with a non-helium auxiliary gas. The auxiliary gas may be hydrogen, nitrogen, or argon.

As described below, the helium gas flow that is established around the end of the analytical capillary column may be provided by a helium gas inlet line that is separate from the carrier gas inlet line and that is configured to supply helium gas so as to flow circumferentially around an exterior surface of the gas chromatography column in a direction generally towards an inlet of the gas chromatography column such that a portion of the helium gas enters the column inlet. The portion of the GC column having the exterior surface around which the helium circumferentially flows may be contained in a short length of pre-column tubing fluidically coupled between the injector and the GC column by a tee-coupling device. The pre-column tubing may comprise a few centimeter length of 0.53 mm inner diameter (ID) fused silica tubing, steel-clad fused silica tubing, glass lined stainless steel tubing, etc. Alternatively, the portion of the GC column having the exterior surface around which the helium circumferentially flows may be contained in a short segment of fused silica tubing that extends into an interior cavity (e.g., a volatilization chamber) of the injector. The fused silica tubing may comprise a deactivated GC column tubing having an inner diameter (ID) that is sufficiently large to contain the active analytical GC column, leaving a space around the analytical column for gas to flow.

Figure 4:
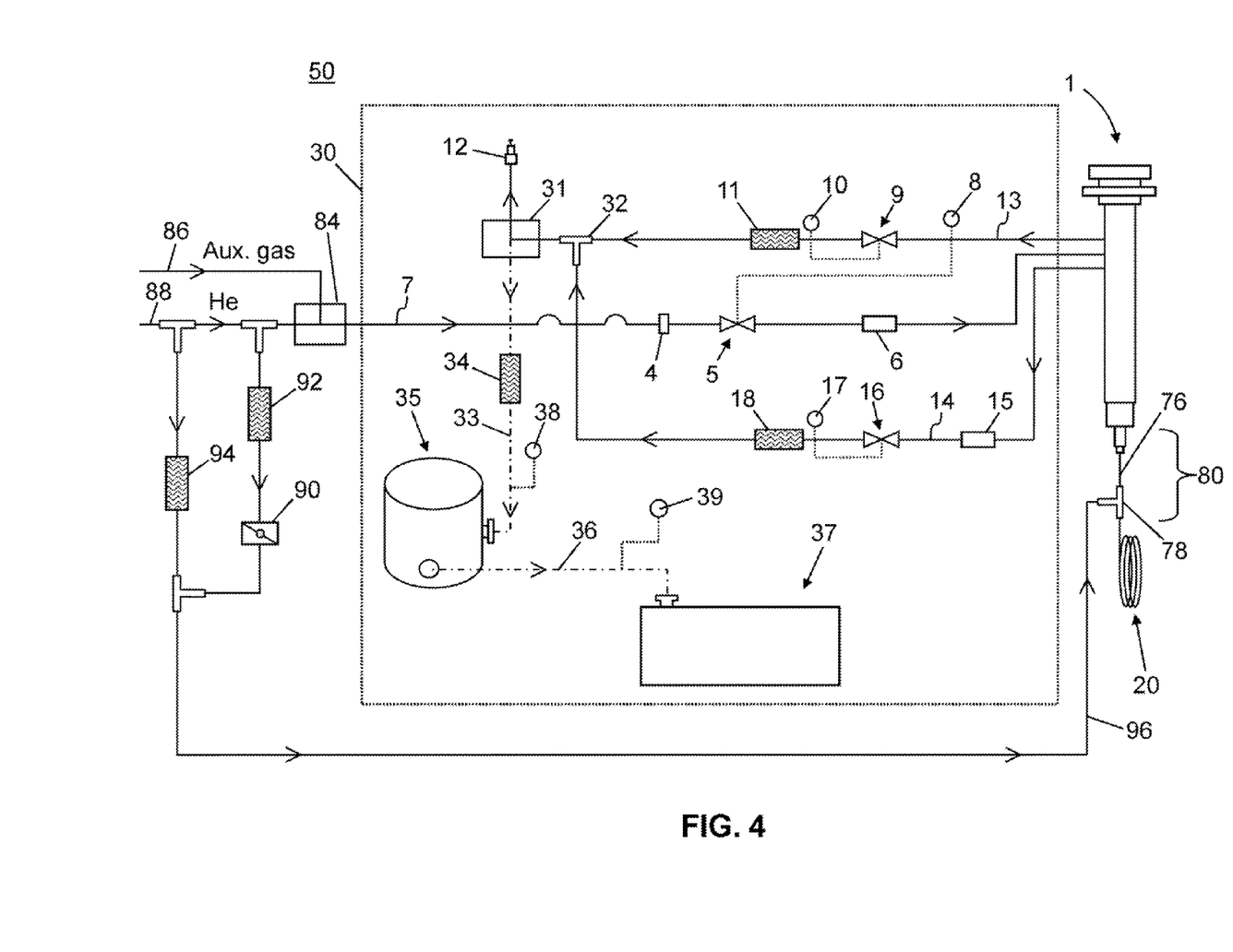
FIG. 4 illustrates a third gas supply and exhaust system for a gas chromatograph in accordance with an embodiment of the present teachings.

FIG. 4 shows a third gas supply and exhaust system for a gas chromatograph in accordance with an embodiment of the present teachings. The system 50 illustrated in FIG. 4 includes a sub-system 30 that is identical to the system 30 shown in FIG. 2. It should be noted that the system 50 could be modified by replacing the sub-system 30 by the sub-systems 41, 42 shown in FIG. 3 and by replacing the illustrated injector 1 by the modified injector 101. The system 50 further includes additional provisions, relative to the above-described embodiments, for supplying a non-helium auxiliary gas and for providing helium from a second inlet so as to establish a helium flow around the inlet end of an analytical column.

In the system 50 (FIG. 4) a conventional injector 1 is modified by outfitting it with a short segment of pre-column 76 and low-dead-volume tee-coupling 78 both of which are disposed within a small heated zone 80. The temperature control of heated zone 80 can be provided by an external controller or by an unused auxiliary heater channel as is often found on typical GC systems. The pre-column 76 is preferably as short as possible and comprises a few centimeter length of 0.53 mm inner diameter (ID) fused silica tubing, steel-clad fused silica tubing, glass lined stainless steel tubing, etc. The inlet of analytical column 20 should preferably pass through the tee-coupling 78 and terminate within the heated pre-column 76, preferably within one centimeter of the end of the pre-column that is closest to the injector. A 3-way selection valve 84, such as a common solenoid valve, allows selection of one of an auxiliary gas from gas line 86 or helium gas from gas line 88. The valve 84 allows (optionally) selection between helium and an auxiliary gas during an injection period. The three-way valve 84 can alternatively comprise a pair of on/off valves if superior isolation between helium and the auxiliary gas is desired.

An on/off type shutoff valve 90, receives a helium flow from gas line 88 via a flow restrictor 92 set to a flow that is above the analytical column flow, such as 2 sccm. The dimensions of the restrictor 92 and another restrictor 94 can be selected based on the input pressure of gas line 88 to establish a given flow range based on the pressure swing of injector 1. The actual flow can vary, e.g. 2-4 sccm without affecting performance. The second flow restrictor 94 is disposed in the flow path of conduit 96 for delivering a low purge flow for compensation of void volume effects. The flow delivered by the capillary restrictor 94 is less than the analytical column flow and can be, for purposes of illustration, 0.05 sccm.

The shutoff valve 90 can be opened to deliver a flow of He that is greater than the column flow (e.g., 2 sccm flow) to the tee-coupling 78 during periods of run time. Otherwise, the valve 90 may be switched off during periods of injection, during cool down of the GC oven, or any non-run time period. Switching of the valve off during non-run time can reduce the helium consumption to nearly zero (0.05) for times when the instrumentation is not being used, utilizing instead the auxiliary gas for column flow. Activation of the valves 84, 90 can be accomplished using the time events programming features of most modern day gas chromatographs.

The helium as flow delivered by the conduit 96 to the tee-coupling 78 can be calculated using a mathematical model, or optimized empirically by adjusting the flow while monitoring, the presence of auxiliary gas in the gas delivered to the column 20. During injection of a sample into the injector 1 of FIG. 4, the flow of helium into conduit 96 can be interrupted by closing the on/off valve 90 such that the delivered helium flow is reduced below the column flow. The auxiliary gas provided from gas line 86 will then sweep sample components onto the analytical column 20. During injection, the flow of He through conduit 96 is preferably reduced to a fraction of the column flow (rather than completely stopped) to a low value e.g. 0.05 sccm to help sweep void volumes, reduce peak tailing and prevent back diffusion of solvent vapors in to the gas lines. Following the injection of the sample and sample transfer to the analytical column 20, the helium flow in conduit 96 is re-established by opening valve 90 so that the chromatographic process utilizes helium within the column for the bulk of the analytical separation, while the auxiliary gas is used to purge the injector.

Figure 5:
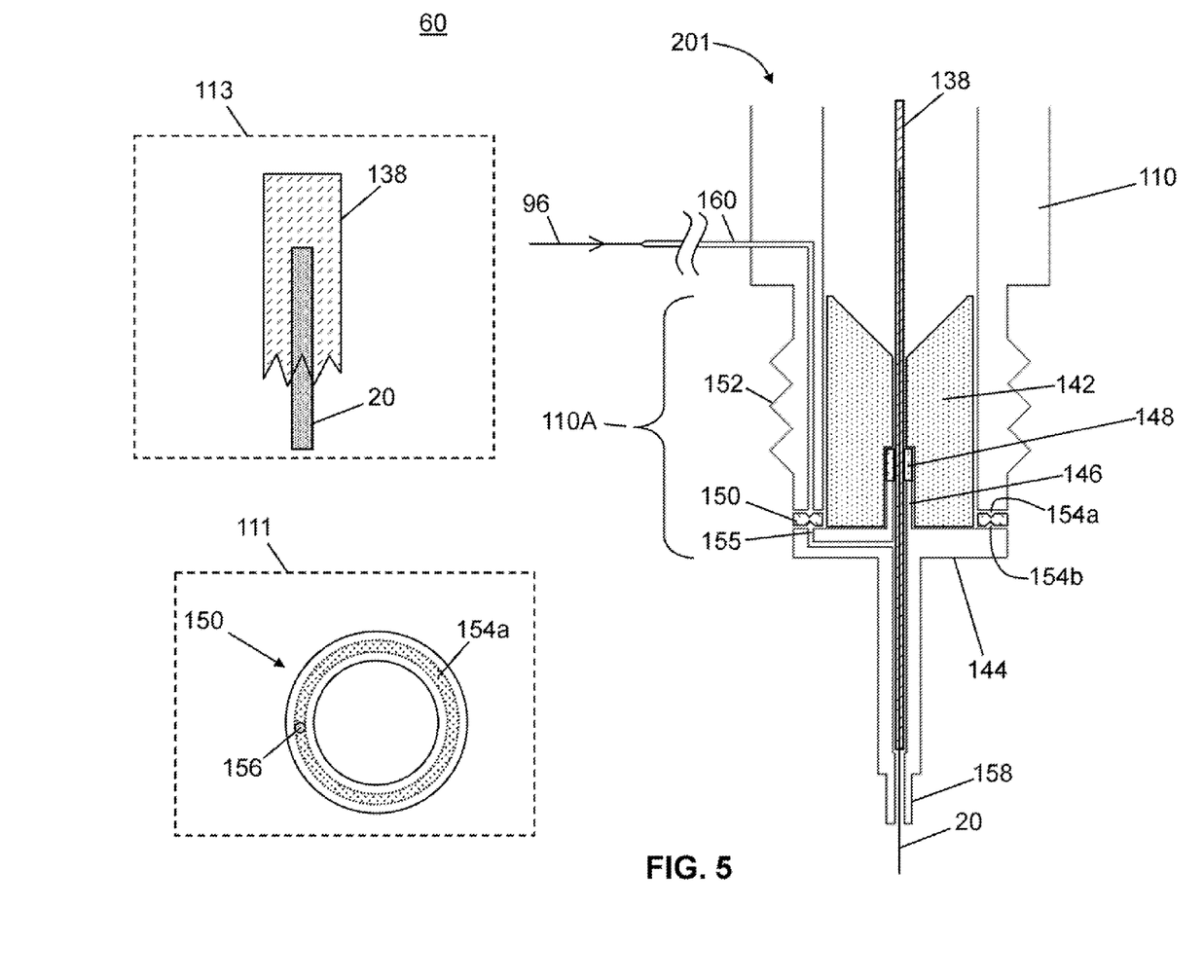
FIG. 5 illustrates a portion of a fourth gas supply and exhaust system for a gas chromatograph in accordance with an embodiment of the present teachings, wherein the system includes a Split/Splitless injector that uses a short narrow bore tube assembly.

FIG. 5 illustrates a portion of a fourth gas supply and exhaust system for a gas chromatograph in accordance with an embodiment of the present teachings. Similarly to the system 50 illustrated in FIG. 4, the system 60, a portion of which is shown in FIG. 5, includes provisions for supplying a non-helium auxiliary gas and for providing helium from a second inlet so as to establish a helium flow around the inlet end of an analytical column.

In the system 60, the lower portion of the SSL injector 201 is modified, relative to a conventional injector, so as to allow helium gas to be selectively passed over the end of an analytical column. The upper end of a conduit 138, e.g. short segment of deactivated fused silica tubing, is positioned within the confines of an injection port liner (not shown). Positioned within the tubing 138 is the analytical column 20 as is shown in the enlargement in inset 113. The short segment of fused silica tubing 138 is selected to have an internal diameter slightly larger than the outer diameter of the analytical column 20. For example, Megabore tubing of 0.53 mm ID is suitable for most analytical columns with internal diameters of 0.25 or 0.32 mm ID. Preferably, the tubing 138 has been deactivated and contains no stationary phase. This segment of tubing alternatively can be fabricated from glass lined stainless steel tubing, Silcosteel™ tubing, or other suitably inert material. In this illustrative example, the analytical column 20 extends preferably to within 1 cm of the uppermost end of the tubing 138. This positioning allows locating the column entrance within the hot injector body, minimizes void volume effects and allows a sufficient back diffusion barrier to the auxiliary gas during analysis.

A liner support 142 and base 144 of the injector 201 are screwed together at the threaded stem 146 to allow compression of an encapsulated graphite ferrule 148. This configuration maintains a gas tight seal between the fused silica tubing 138 and the base 144. A soft metallic gasket 150 is positioned between the base 144 and terminal end 110A of the injector body 110 to create a seal between base 144 and the injector body 110. A retaining nut (not shown) secures the base 144 to the threaded portion 152 of injector body 110.

The gasket 150 of the injector 201 of the system 60 (FIG. 5) includes a pair of gas channels 154a, 154b in the form of annular grooves cut on each face of the metallic gasket 150. The gasket 150 shown in top view in inset 111 also includes a hole 156 located on the centerline of gasket 150 to create a fluid communication between the upper and lower groove channels 154a, 154b. The terminal end 158 of base 144 is threaded so that a retaining nut and ferrule (not shown for simplicity) can create a seal between the analytical column 20 and the base 144. A conduit 160 fluidically coupled to gas line 96 supplies a flow of helium to the upper groove channel 154a. The helium flows around the upper groove channel 154a until it finds hole 156. It then passes through hole 156 into the lower groove channel 154b and into base 144 at entrance point 155. The base 144 allows the helium to flow downward around the outside of the fused silica tube 138 to sweep void volume then proceed upward into tube 138 and finally injector the injector interior after passing the input end of the analytical column 20. After sample injection, the flow established into the conduit 160 should be slightly higher than the calculated column flow delivered to column 20 following the injection period. To illustrate, 2 sccm of conduit flow could be used for calculated column flows of 1 sccm. In this illustrative example (FIG. 5), the conduit 160 may comprise a 304 stainless steel tube of 0.9 mm outer diameter (OD), 0.5 mm ID and 300 mm length. The conduit is attached to the hot injector body 110.

By combining an injector inlet evacuation system (e.g., FIGS. 2-3) with the ability to provide an auxiliary non-helium purge and split flow as well as a separate helium flow surrounding the column entrance (e.g., FIGS. 4-5), flexibility in gas conservation is achieved. A user may use the helium conservation techniques described in the aforementioned U.S. Pat. No. 8,371,152 during sample injections and between injections when samples are being analyzed in order to conserve helium carrier gas. Additionally, a user may employ the injector evacuation techniques taught herein when the gas chromatograph is placed into standby or idle mode, thereby conserving all gases.

Additionally, if it is desired to maintain the gas chromatograph column at its normal operating temperature during a standby period, then the injector evacuation techniques may be employed in conjunction with the technique of providing of a low flow of helium gas around and into the column entrance from a separate inlet. Providing a protective flow of helium gas in such a fashion can enable the column to remain hot during idle periods, while the injector interior is under partial vacuum, without incurring column degradation. It may be desirable to maintain the gas chromatograph column at its normal operating temperature if the column is one of a set of columns whose separate eluates are directed to a single detector such as, for example two separate columns coupled to a single ionization source of a mass spectrometer. Such a system may permit alternating analyses of samples provided from each column. In such a system, one column may be placed in standby mode for an extended period of time while a second column is supplying, material to be analyzed by the detector.

Figure 6:
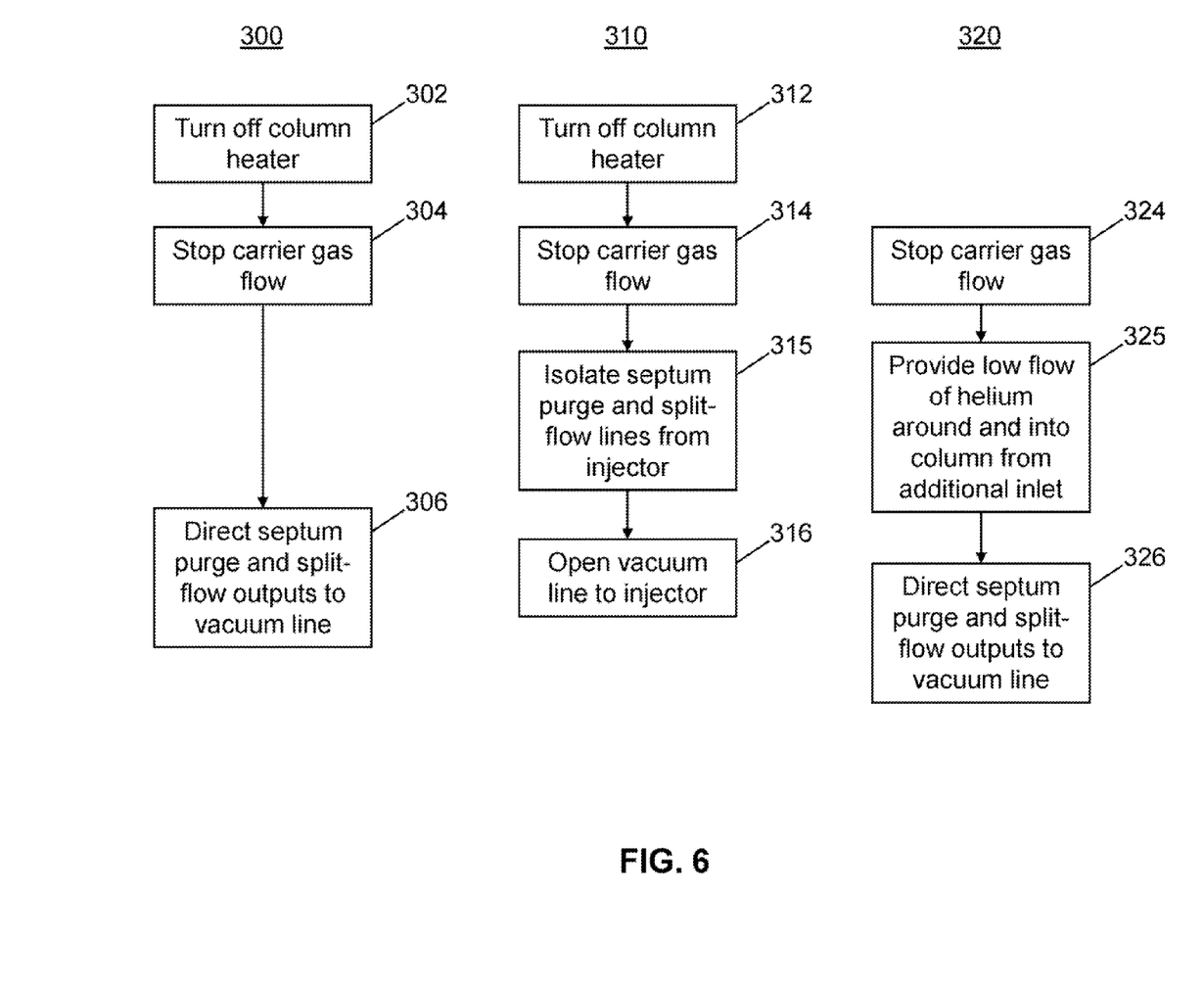
FIG. 6 is a set of flow diagrams of three exemplary methods in accordance with the present teachings.

FIG. 6 provides, in flow diagram form, a comparison of three exemplary methods for operating a gas chromatograph in accordance with the present teachings. Method 300 may be employed, for example, in conjunction with the system 30 of FIG. 2 or a similar system. In step 302, the column heater (typically an oven within which the column is disposed) is turned off and the column is allowed to cool. Then, in step 304, the flow of carrier gas (typically helium) is stopped. This step may be accomplished, for example, by closing a valve, such as proportional valve 5 in FIG. 2, that controls flow of the carrier gas into an inlet line. Subsequently, in step 306, the output flows of the septum purge and split-flow lines are directed to a vacuum line so as to evacuate these lines as well as the injector. This step may be performed, for example, by reconfiguring the three-port valve, three-port valve 31) so that flow through both of the lines 13 and 14 is directed into the vacuum line 33. This set of steps may be used to place a gas chromatograph system into standby or idle mode. To return the system to normal operation, the sequence of steps may be reversed, with each such step in the reverse procedure performing an opposite function to that shown in FIG. 6 (e.g., instead of turning off the column heater as illustrated in the diagram, turn on the column heater in the reversed procedure).

Method 310 is similar to step 300 (steps 312 and 314 of method 310 are identical to steps 302 and 304, respectively, of the method 300) and may be employed in conjunction with system 30 of FIG. 3 or a similar system that comprises a separate vacuum sub-system having a dedicated vacuum line to an injector. In step 315, the septum purge vent line and split-flow vent lines are isolated from the injector (that is, removed from being in fluidic communication with the injector interior) by, for example, closing shutoff valves 43 and 44 in FIG. 3. Subsequently, in step 316, the injector is exposed to vacuum by, for example, opening a valve (e.g., shutoff valve 45) on a vacuum line (e.g., line 33) that leads to a dedicated port (e.g., port 33p) of the injector inlet. This set of steps may be used to place a gas chromatograph system into standby or idle mode. To return the system to normal operation, the sequence of steps may be reversed, with each such step in the reverse procedure performing an opposite function to that shown in FIG. 3.

Method 320 is applicable, for example, to a system, such as system 40 illustrated in FIG. 4 that combines an evacuable injector inlet with in conjunction with a provision for supplying a low flow of helium gas around and into the column entrance from a separate inlet. The chromatographic column is allowed to remain at its operating temperature during practice of the method 320. In step 324, the flow of purge as (either helium or an auxiliary gas such as nitrogen or argon) is stopped. Then, in step 325, a low flow of protective helium is provided (if not flowing already) around the column from an additional gas inlet so as to flow into the column. The flow rate from the additional gas inlet is slightly above the nominal column flow rate such as, for example one-and-one-half times the column flow rate or twice the flow rate. Subsequently, in step 326, the output flows of the septum purge and split-flow lines are directed to a vacuum line so as to evacuate these lines as well as the injector. The low flow rate of helium into the column prevents degradation of the column at high temperature but does not significantly degrade the vacuum within the injector interior. This set of steps may be used to place a gas chromatograph system into standby or idle mode. To return the system to normal operation, the sequence of steps may be reversed, with each such step in the reverse procedure performing an opposite function to that shown in FIG. 6.

The discussion included in this application is intended to serve as a basic description. Although the present invention has been described in accordance with the various embodiments shown and described, one of ordinary skill in the art will readily recognize that there could be variations to the embodiments and those variations would be within the scope of the present invention. The reader should be aware that the specific discussion may not explicitly describe all embodiments possible; many alternatives are implicit. Accordingly, many modifications may be made by one of ordinary skill in the art without departing from the scope of the invention. Neither the description nor the terminology is intended to limit the scope of the invention—the invention is defined only by the claims. Any patents, patent publications or other publications mentioned herein are hereby incorporated by reference in their respective entireties.

What is claimed is:

1. A gas chromatography (GC) system comprising:
    a sample injector adapted to receive a liquid sample into an interior cavity thereof and to volatilize the liquid sample;
    a GC column configured to receive the volatilized sample from the sample injector, wherein the sample injector is configurable to perform either split injection or splitless injection into the GC column;
    a carrier gas inlet line fluidically coupled to a gas inlet port of the sample injector;
    a septum purge vent line fluidically coupled to a first gas outlet port of the sample injector;
    a split-flow vent line fluidically coupled to a second gas outlet port of the sample injector; and
    a vacuum system configured to place the septum purge vent line, the split-flow vent line and the interior cavity of the sample injector under vacuum.

2. A gas chromatography system as recited in claim 1, wherein an output of the septum purge vent line and an output of the split-flow vent line are both switchable so as to be directed either to the vacuum system or to an exhaust port.

3. A gas chromatography system as recited in claim 2, wherein the septum purge vent line and the split-flow vent line are both fluidically coupled to a common port of a three-way valve, wherein the vacuum system is fluidically coupled to a second port of the three-way valve and wherein the exhaust port is coupled to a third port of the three-way valve.

4. A gas chromatography system as recited in claim 1, wherein the vacuum system comprises:
    a vacuum line having first and second ends, the first end fluidically coupled to both of the septum purge vent line and the split-flow vent line;
    a high-vacuum pump having an input port fluidically coupled to the second end of the vacuum line and a foreline port;
    a roughing vacuum pump; and
    a foreline vacuum line fluidically coupled between the foreline port of the high-vacuum pump and an input port of the roughing vacuum pump.

5. A gas chromatography system as recited in claim 4, wherein the vacuum system further comprises:
    a sensor configured to measure a vacuum pressure within the foreline vacuum line; and
    an electronic controller electronically coupled to both the sensor and the roughing vacuum pump and configured to switch the roughing pump into either an on state or an off state depending on the measured foreline vacuum pressure.

6. A gas chromatography system as recited in claim 1, further comprising a helium gas inlet line configured to supply helium gas so as to flow circumferentially around an exterior surface of the GC column in a direction generally towards an inlet of the gas chromatography column such that a portion of the helium gas enters the column inlet.

7. A gas chromatography system as recited in claim 3, further comprising an electronic controller electronically coupled to the three-way valve and to a shutoff valve disposed within the helium gas inlet line and configured to activate the helium gas flow when the septum purge vent line, the split-flow vent line and the interior cavity of the sample injector are under vacuum.

8. A gas chromatography system as recited in claim 6, further comprising a selection valve fluidically coupled to the carrier gas inlet line, to a source of helium gas and to a source of non-helium gas, such that carrier gas provided to the sample injector by means of the carrier gas inlet line is selectable between the helium and the non-helium gas.

9. A gas chromatography (GC) system comprising:
    a sample injector adapted to receive a liquid sample into an interior cavity thereof and to volatilize the liquid sample;
    a GC column configured to receive the volatilized sample from the sample injector, wherein the sample injector is configurable to perform either split injection or splitless injection into the GC column;
    a carrier gas inlet line fluidically coupled to a first port of the sample injector, said first port comprising a carrier gas inlet port;
    a septum purge vent line fluidically coupled to a second port of the sample injector, said second port comprising a first gas outlet port;
    a split-flow vent line fluidically coupled to a third port of the sample injector, said third port comprising a second gas outlet port; and
    a vacuum system fluidically coupled to a fourth port of the sample injector, said fourth port comprising a vacuum port.

10. A gas chromatography system as recited in claim 9, wherein the vacuum system comprises:
    a vacuum line having first and second ends, the first end fluidically coupled to the vacuum port of the sample injector;

a high-vacuum pump having an input port fluidically coupled to the second end of the vacuum line and a foreline port;

a roughing vacuum pump; and a foreline vacuum line fluidically coupled between the foreline port of the high-vacuum pump and an input port of the roughing vacuum pump.

11. A gas chromatography system as recited in claim 10, wherein the vacuum system further comprises:

a sensor configured to measure the vacuum pressure within the foreline vacuum line; and an electronic controller electronically coupled to both the sensor and the roughing vacuum pump and configured to switch the roughing pump to either an on state or an off state depending on the measured foreline vacuum pressure.

12. A gas chromatography system as recited in claim 9, further comprising a shutoff valve disposed between the vacuum system and the vacuum port of the sample injector and operable to isolate the vacuum system from the sample injector during sample injections.

13. A gas chromatography system as recited in claim 9, further comprising a shutoff valve disposed in the septum purge vent line and another shutoff valve disposed in the split-flow vent line, said shutoff valves respectively operable to prevent the vacuum system from applying vacuum to the septum purge vent line and the split-flow vent line.

14. A gas chromatography system as recited in claim 9, further comprising a helium gas inlet line configured to supply helium gas so as to flow circumferentially around an exterior surface of the GC column in a direction generally towards an inlet of the GC column such that a portion of the helium gas enters the GC column inlet.

15. A gas chromatography system as recited in claim 14, further comprising a selection valve fluidically coupled to the carrier gas inlet line, to a source of helium gas and to a source of non-helium gas, such that carrier gas provided to the sample injector by means of the carrier gas inlet line is selectable between the helium and the non-helium gas.

16. A method for operating a gas chromatography (GC) system comprising (a) a GC column within a heating oven and (b) a sample injector fluidically coupled to the GC column and having a carrier gas inlet port, a septum purge outlet port and a split-flow outlet port such that the sample injector is configurable to perform either split injection or splitless injection into the GC column, the method comprising:

(i) discontinuing heating of the GC column by the heating oven;

(ii) discontinuing the flow of a carrier gas into the carrier gas inlet port; and (iii) directing outputs of the septum purge outlet port and the split-flow vent outlet port to a vacuum system such that an interior cavity of the sample injector is placed under vacuum.

17. A method for operating a gas chromatography system as recited in claim 16, further comprising:

(iv) providing helium gas so as to flow circumferentially around an exterior surface of the GC column in a direction generally towards an inlet of the GC column such that a portion of the helium gas enters the column inlet.

18. A method for operating a gas chromatography (GC) system comprising (a) a GC column within a heating oven and (b) a sample injector fluidically coupled to the GC column and having a first port comprising a carrier gas inlet port, a second port comprising a septum purge outlet port, a third port comprising a split-flow outlet port and a fourth port comprising a vacuum port, wherein the sample injector is configurable to perform either split injection or splitless injection into the GC column, the method comprising:

(i) discontinuing heating of the GC column by the heating oven;

(ii) discontinuing a flow of a carrier gas into the carrier gas inlet port;

(iii) closing the septum purge outlet port and the split-flow vent outlet port so as to prevent gas flow therethrough; and (iv) putting the vacuum port into fluidic communication with a vacuum system such that an interior cavity of the sample injector is placed under vacuum.

19. A method for operating a gas chromatography system as recited in claim 18, further comprising:

(v) providing helium gas so as to flow circumferentially around an exterior surface of the GC column in a direction generally towards an inlet of the GC column such that a portion of the helium gas enters the column inlet.

20. A method for operating a gas chromatography (GC) system comprising (a) a GC column within a heating oven and (b) a sample injector fluidically coupled to the GC column and having a carrier gas inlet port, a septum purge outlet port and a split-flow outlet port such that the sample injector is configurable to perform either split injection or splitless injection into the GC column, the method comprising:

(i) discontinuing the flow of a carrier gas into the carrier gas inlet port;

(ii) directing outputs of the septum purge outlet port and the split-flow vent outlet port to a vacuum system such that an interior cavity of the sample injector is placed under vacuum, wherein the heating oven is maintained at an above-ambient operating temperature; and (iii) providing helium gas so as to flow circumferentially around an exterior surface of the GC column in a direction generally towards an inlet of the GC column such that a portion of the helium gas enters the column inlet.

21. A method for operating a gas chromatography system as recited in claim 20, wherein a flow rate of the helium gas is sufficient to prevent degradation of the GC column at the operating temperature but insufficient to prevent maintenance of vacuum within the interior cavity of the sample injector.

22. A gas chromatography (GC) system comprising: a sample injector adapted to receive a liquid sample into an interior cavity thereof from a syringe inserted through a septum and to volatilize the liquid sample; a GC column configured to receive the volatilized sample from the sample injector; a carrier gas inlet line fluidically coupled to a gas inlet port of the sample injector; a septum purge vent line fluidically coupled to a first gas outlet port of the sample injector; a split-flow vent line fluidically coupled to a second gas outlet port of the sample injector; and a vacuum system configured to place the septum purge vent line, the split-flow vent line and the interior cavity of the sample injector under vacuum.

23. A gas chromatography system as recited in claim 22, wherein an output of the septum purge vent line and an output of the split-flow vent line are both switchable so as to be directed either to the vacuum system or to an exhaust port.

24. A gas chromatography system as recited in claim 23, wherein the septum purge vent line and the split-flow vent line are both fluidically coupled to a common port of a three-way valve, wherein the vacuum system is fluidically coupled to a second port of the three-way valve and wherein the exhaust port is coupled to a third port of the three-way valve.

25. A gas chromatography system as recited in claim 22, wherein the vacuum system comprises:

a vacuum line having first and second ends, the first end fluidically coupled to both of the septum purge vent line and the split-flow vent line;

a high-vacuum pump having an input port fluidically coupled to the second end of the vacuum line and a foreline port;

a roughing vacuum pump; and a foreline vacuum line fluidically coupled between the foreline port of the high-vacuum pump and an input port of the roughing vacuum pump.

26. A gas chromatography system as recited in claim 25, wherein the vacuum system further comprises:

a sensor configured to measure a vacuum pressure within the foreline vacuum line; and an electronic controller electronically coupled to both the sensor and the roughing vacuum pump and configured to switch the roughing pump into either an on state or an off state depending on the measured foreline vacuum pressure.

27. A gas chromatography system as recited in claim 22, further comprising a helium gas inlet line configured to supply helium gas so as to flow circumferentially around an exterior surface of the GC column in a direction generally towards an inlet of the gas chromatography column such that a portion of the helium gas enters the column inlet.

28. A gas chromatography system as recited in claim 24, further comprising an electronic controller electronically coupled to the three-way valve and to a shutoff valve disposed within the helium gas inlet line and configured to activate the helium gas flow when the vacuum is applied to the septum purge vent line, the split-flow vent line and the interior cavity of the sample injector.

29. A gas chromatography system as recited in claim 27, further comprising a selection valve fluidically coupled to the carrier gas inlet line, to a source of helium gas and to a source of non-helium gas, such that carrier gas provided to the sample injector by means of the carrier gas inlet line is selectable between the helium and the non-helium gas.

\* \* \* \* \*